United States Patent
Yan et al.

(10) Patent No.: US 10,697,929 B2
(45) Date of Patent: Jun. 30, 2020

(54) ACTIVE NOISE CONTROL BIOSENSOR

(71) Applicant: NANJING UNIVERSITY, Nanjing, Jiangsu (CN)

(72) Inventors: Feng Yan, Jiangsu (CN); Cheng Mao, Jiangsu (CN); Limin Zhang, Jiangsu (CN); Cheng Yang, Jiangsu (CN); Xiaofeng Bu, Jiangsu (CN); Haowen Ma, Jiangsu (CN)

(73) Assignee: NANJING UNIVERSITY, Nanjing, Jiangsu (CN)

( * ) Notice: Subject to any disclaimer, the term of this patent is extended or adjusted under 35 U.S.C. 154(b) by 17 days.

(21) Appl. No.: 16/322,427

(22) PCT Filed: Oct. 20, 2016

(86) PCT No.: PCT/CN2016/102689
§ 371 (c)(1),
(2) Date: Jan. 31, 2019

(87) PCT Pub. No.: WO2018/032600
PCT Pub. Date: Feb. 22, 2018

(65) Prior Publication Data
US 2019/0195826 A1    Jun. 27, 2019

(30) Foreign Application Priority Data
Aug. 15, 2016   (CN) .......................... 2016 1 0669750

(51) Int. Cl.
*G01N 27/403*    (2006.01)
*G01N 27/414*    (2006.01)
(Continued)

(52) U.S. Cl.
CPC ......... *G01N 27/4145* (2013.01); *G01N 33/50* (2013.01); *G10K 11/175* (2013.01); *G01N 27/4148* (2013.01)

(58) Field of Classification Search
CPC ..... H04L 67/12; H04L 1/0002; H04L 1/0041; H04L 1/18; H04L 5/0064; H04L 67/1097;
(Continued)

(56) References Cited

U.S. PATENT DOCUMENTS

2018/0011053 A1*   1/2018   Hadwen ............. G01N 27/4145

FOREIGN PATENT DOCUMENTS

WO      1995035548 A1    12/1995

* cited by examiner

*Primary Examiner* — Robert G Bachner
(74) *Attorney, Agent, or Firm* — Novick, Kim & Lee, PLLC; Allen Xue

(57) ABSTRACT

Provided is a novel active noise control biosensor including a detection plate, a signal detection module and a control module. The signal detection module includes a signal superimposable transistor and a readout circuit. The signal superimposable transistor has a secondary input terminal and a primary input terminal. The detection plate inputs a detected primary signal to the primary input terminal, and the control module processes an output signal from the signal detection module by a signal processing system and generates and inputs a secondary signal to the secondary input terminal. The primary signal and the secondary signal received by the signal superimposable transistor are superimposed to realize active noise control, and the superimposed signal is read out by the readout circuit and output as an input signal to the control module. The biosensor can achieve the detection of potential or charges and have active noise control characteristics.

16 Claims, 9 Drawing Sheets

(51) Int. Cl.
*G01N 33/50* (2006.01)
*G10K 11/175* (2006.01)

(58) Field of Classification Search
CPC .......... G06N 20/00; G06N 3/02; G06N 3/006;
G06N 3/0445; G06N 3/0454; G06N
3/0472; G06N 3/084; G06N 3/088; G06N
3/126; G06N 5/046; G06N 7/005; G05B
13/028; G05B 19/4183; G05B 19/4184;
G05B 19/41845; G05B 19/4185; G05B
19/41865; G05B 19/41875; G05B
2219/32287; G05B 2219/35001; G05B
2219/37337; G05B 2219/37351; G05B
2219/37434; G05B 2219/40115; G05B
2219/45004; G05B 2219/45129; G05B
23/0221; G05B 23/0229; G05B 23/024;
G05B 23/0264; G05B 23/0283; G05B
23/0286; G05B 23/0289; G05B 23/0291;
G05B 23/0294; G05B 23/0297; G06K
9/6263; G06K 9/00255; G06K 9/00261;
G06K 9/00281; G06K 9/00315; G06K
9/00335; G06K 9/00342; G06K 9/00369;
G06K 9/00664; G06K 9/00671; G06K
9/00845; G06K 9/00892; G06K 9/2036;
G06K 9/209; G06K 9/6293; G06K 9/72;
H04B 17/309; H04B 17/318; H04B
5/0031; H04B 5/0037; Y02P 80/114;
Y02P 90/02; G01N 27/4145; G01N
27/4146; G01N 33/54373; G01N
33/5438; G01N 27/4148; G01N
33/48792; G01N 33/54346; G01N
21/6428; G01N 21/6454; G01N 21/7703;
G01N 27/3278; G01N 33/5308; G01N
33/54366; G01N 33/56911; G01N
33/588; G01N 15/1404; G01N 15/1429;
G01N 1/28; G01N 2015/145; G01N
2021/5903; G01N 2021/6439; G01N
2021/6441; G01N 2021/7779; G01N
2035/00326; G01N 2035/00495; G01N
2035/00881; G01N 2035/0094; G01N
21/00; G01N 21/4133; G01N 21/45;
G01N 21/47; G01N 21/553; G01N
21/554; G01N 21/59; G01N 21/61; G01N
21/658; G01N 21/763; G01N 21/77;
G01N 21/7746; G01N 2333/90241; G01N
2333/904; G01N 2333/90638; G01N
27/12; G01N 27/125; G01N 27/227;
G01N 27/27; G01N 27/301; G01N
27/302; G01N 27/327; G01N 27/3272;
G01N 27/3275; G01N 27/333; G01N
27/4065; G01N 27/4071; G01N 27/4141;
G01N 27/417; G01N 27/44791; G01N
27/453; G01N 2800/00; G01N 33/0006;
G01N 33/0031; G01N 33/48721; G01N
33/542; G01N 33/54306; G01N
33/54313; G01N 33/54333; G01N
33/54353; G01N 33/54386; G01N
33/552; G01N 33/56983; G01N
33/57415; G01N 33/582; G01N 33/64;
G01N 33/9406; G01N 33/9413; G01N
35/00871; G01N 35/0092; G01N
35/0098; G01N 35/026; G01N 35/10;
G01N 35/1065

See application file for complete search history.

ACTIVE NOISE CONTROL BIOSENSOR

TECHNICAL FIELD OF THE INVENTION

The present invention relates to a bioelectrical activity detection sensor which can be widely applied in biomedical and other technical applications, such as cell activity detection, DNA detection, bioprotein detection and drug screening. Different implementations of the present invention can be used for voltage signal detection and charge signal detection.

BACKGROUND OF THE INVENTION

Recently, the biological molecular process detection has attracted more and more attention, for example, cell activity detection, DNA detection, bioprotein detection, drug screening and so on. Compared with the optical detection, the direct electrical activity detection is simple in operation and convenient for in-vivo detection. At present, the direct electrical activity detection mainly uses two conventional solid-state biosensors, i.e., a microelectrode array and a field effect device. However, in the two conventional sensors, an additional reference electrode is needed for setting a difference in voltage between a solution and a substrate of the sensor. As a result, it is difficult to realize large-scale integration in a standard integrated circuit process of conventional sensors, and the further reduction in cost and development in portability of such sensors are hindered.

As a common basic unit in a semiconductor device, a floating gate transistor has two ports, i.e., a floating gate and a control gate, which both may be used as an input terminal. Meanwhile, the control of the turn-on voltage and the saturation current may be realized by a superposition principle of the control gate and the floating gate. Therefore, some scholars have proposed devices structurally similar to floating gate transistors. The use of the control gate makes up the deficiency that the conventional sensors require additional reference electrodes. However, the control gate can only be used to set a quiescent operating point. During the actual detection, there are electrochemical noise caused by the ionic movement of an electrolyte solution, slow DC drift caused by the change in temperature, and so on. The noise will inhibit or hinder accurate signal detection, so it is necessary to provide a novel sensor to overcome this noise, make up the deficiencies of the existing sensors and realize high signal-to-noise ratio detection.

SUMMARY OF THE INVENTION

To overcome the deficiencies in the prior art, the present invention provides a novel sensor on the basis of an active noise control principle and a signal superimposition principle. The sensor can achieve the detection of potential or charges and have active noise control characteristics; and, the sensor not only can achieve detection without any reference electrode, and can also effectively inhibit the slow DC drift, harmonic noise and broadband noise during detection and realize high signal-to-noise ratio detection.

The present invention employs the following technical solutions.

A novel active noise control biosensor is provided, including a detection plate, a signal detection module and a control module, characterized in that the signal detection module includes a signal superimposable transistor and a readout circuit; the signal superimposable transistor has at least two input terminals, including a secondary input terminal for receiving a secondary signal and a primary input terminal for receiving a primary signal; the detection plate inputs a detected primary signal to the primary input terminal, and the control module processes an output signal from the signal detection module by a signal processing system and generates and inputs a secondary signal to the secondary input terminal; and, the primary signal and the secondary signal received by the signal superimposable transistor are superimposed to realize active noise control, and the superimposed signal is read out by the readout circuit and output as an input signal to the control module.

A gate of the signal superimposable transistor is connected to a capacitor and a metal wire serving as a secondary input terminal and a primary input terminal; or, the gate of the transistor is connected to two capacitors serving as a primary input terminal a secondary input terminal.

Further, the signal superimposable transistor is a field effect transistor.

As another technical solution, on a substrate of the signal superimposable transistor, two heavily doped regions are generated as a source and a drain, respectively; a double-gate structure is provided above the substrate, with the first gate layer being a floating gate and the second gate layer being a control gate; the lower portion of the floating gate is isolated from the substrate by a dielectric layer, while the upper portion thereof is isolated from the control gate by another dielectric layer; and, the floating gate is connected to the detection plate by a metal wire to serve as a primary input terminal, and the control gate serves as a secondary input terminal.

As another technical solution, on a substrate of the signal superimposable transistor, two heavily doped regions are generated as a source and a drain, respectively; a double-gate structure is provided above the substrate, the first gate layer is a floating gate, and the second gate layer is a split gate structure including a control gate and a floating gate coupled input terminal between which an isolation layer is provided; a lower portion of the floating gate is isolated from the substrate by a dielectric layer while an upper portion thereof is isolated from the second gate layer by another dielectric layer; and, the floating gate coupled input terminal is connected to the detection plate by a metal wire to serve as a primary input terminal, and the control gate serves as a secondary input terminal.

As another technical solution, on a substrate of the signal superimposable transistor, two heavily doped regions are generated as a source and a drain, respectively; a single-gate structure as a floating gate is provided above the substrate; the floating gate is isolated from the substrate by a dielectric layer; the floating gate is connected to two metal-insulating layer-metal capacitors serving as a primary input terminal and a secondary input terminal.

As another technical solution, on a substrate of the signal superimposable transistor, two heavily doped regions are generated as a source and a drain, respectively; a single-gate structure as a floating gate is provided above the substrate; a well is generated on a side of the substrate in a gate width direction; an isolation layer is provided between the substrate and the well, and the floating gate is isolated from the well and the substrate by a dielectric layer; the well serves as a secondary input terminal and the floating gate is connected to the detection plate by a metal wire to serve as a primary input terminal; or, the well serves as a secondary input terminal and the floating gate is connected to a metal-insulating layer-metal capacitor to serve as a primary input terminal; or, the well serves as a primary input terminal and the floating gate is connected to a metal-insulating layer-metal capacitor to serve as a secondary input terminal.

As another technical solution, on a substrate of the signal superimposable transistor, two heavily doped regions are generated as a source and a drain, respectively; a single-gate structure as a floating gate is provided above the substrate; two wells are generated on a side of the substrate in a gate width direction to serve as a control gate and a floating gate coupled input terminal, respectively; an isolation layer is provided between the substrate and the wells, and the floating gate is isolated from the wells and the substrate by a dielectric layer; and, the floating gate coupled input terminal is connected to the detection plate by a metal wire to serve as a primary input terminal, and the control gate serves as a secondary input terminal.

The control module is a no-reference feedforward control module, that is, a harmonic signal having a known frequency is directly generated inside the control module as a reference for feedforward control, and an output signal from the signal detection module is processed by feedforward control to generate and input a secondary input signal to the secondary input terminal of the signal detection module; or, the control module is a reference feedforward control module, that is, a reference noise input terminal is drawn from the control module to detect background noise as a reference for feedforward control, and an output signal from the signal detection module is processed by feedforward control to generate and input a secondary input signal to the secondary input terminal of the signal detection module; or, the control module is a feedback control module, and an output signal from the signal detection module is processed by feedback control to generate and input a secondary signal to the secondary input terminal of the signal detection module.

The novel active noise control biosensor of the present invention has the following remarkable advantages.

(1) The biosensor can achieve the detection of potential or charges. The charge detection can be achieved when the gate of the signal superimposable transistor is directly connected to the detection plate by a wire, and the potential detection can be achieved when the gate of the signal superimposable transistor is connected to the detection plate by a capacitor.

(2) The signal superimposable transistor has a secondary input terminal for receiving a secondary input terminal and a primary input terminal for receiving a primary signal, so the control of output signals (including the control of DC and AC) can be flexibly realized by the superimposition of two or more input terminals.

(3) The control module can effectively suppress the slow DC drift, harmonic noise and broadband noise by feedforward control or feedback control, and the control mode is flexible.

(4) The biosensor not only can achieve detection without any reference electrode, and can also effectively inhibit the slow DC drift, harmonic noise and broadband noise during detection and realize high signal-to-noise ratio detection.

BRIEF DESCRIPTION OF THE DRAWINGS

FIG. 1A shows a transistor having a direct-input-type primary input terminal, and FIG. 1B shows a transistor having a primary input terminal with a capacitor;

DETAILED DESCRIPTION OF THE INVENTION

To make the contents of the present invention clearer, the implementations of the present invention will be further described below with reference to the accompanying drawings.

Figure 1A:
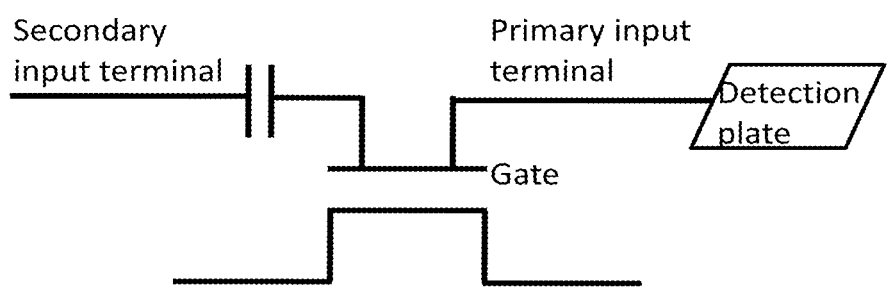
FIGS. 1A and 1B are schematic diagrams of two different structures of a signal superimposable transistor according to the present invention, where
Figure 1B:
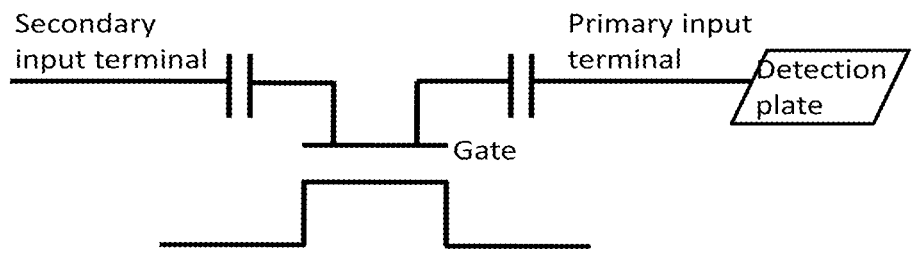

FIGS. 1A and 1B show a schematic structure diagrams of a signal superimposable transistor as a core device according to the present invention. The present invention provides two signal superimposable transistors of different structures. Theoretically, the signal superimposable transistor may be interpreted as a transistor with a gate controlled by at least two input terminals. One input terminal is a secondary input terminal which realizes the regulation of the gate by a capacitor, and the other input terminal is a primary input terminal which may directly control the transfer of charges by a metal wire so as to realize the regulation of the gate, as shown in FIG. 1A, or may realize the regulation of the gate by a capacitor, as shown in FIG. 1B. In the present invention, a primary signal and a secondary signal are input mainly by the two input terminals, and the noise in the two input signals is superimposed and cancelled out so as to realize active noise control. For ease of description, the signal superimposable transistor 101 of FIG. 1A is called a transistor having a direct-input-type primary input terminal, and the signal superimposable transistor 102 of FIG. 1B is a transistor having a primary input terminal with a capacitor. The two transistors are used for charge detection and potential detection, respectively.

The devices based on the two principles shown in FIGS. 1A and 1B may be implemented in various forms. The most basic method is to use a basic field effect transistor, wherein the gate is connected to a capacitor and a wire serving as a secondary input terminal and a primary input terminal, corresponding to the principle in FIG. 1A; or, the gate is connected to two capacitors serving as a primary input terminal and a secondary input terminal, corresponding to the principle in FIG. 1B. However, the internal integral is difficulty realized by this method. A more ingenious method that can realize the internal integration of the capacitor will be described below. As a common basic unit in a semiconductor device, a floating gate transistor has two ports, i.e., a floating gate and a control gate, which both may be used as an input terminal. Meanwhile, the control of the turn-on voltage and the saturation current may be realized by a superposition principle of the control gate and the floating gate. The present invention will provide several floating gate transistor analogues to realize a signal superimposable transistor. The detailed description will be given below by several specific implementations with reference to FIGS. 2-5C.

Figure 2:
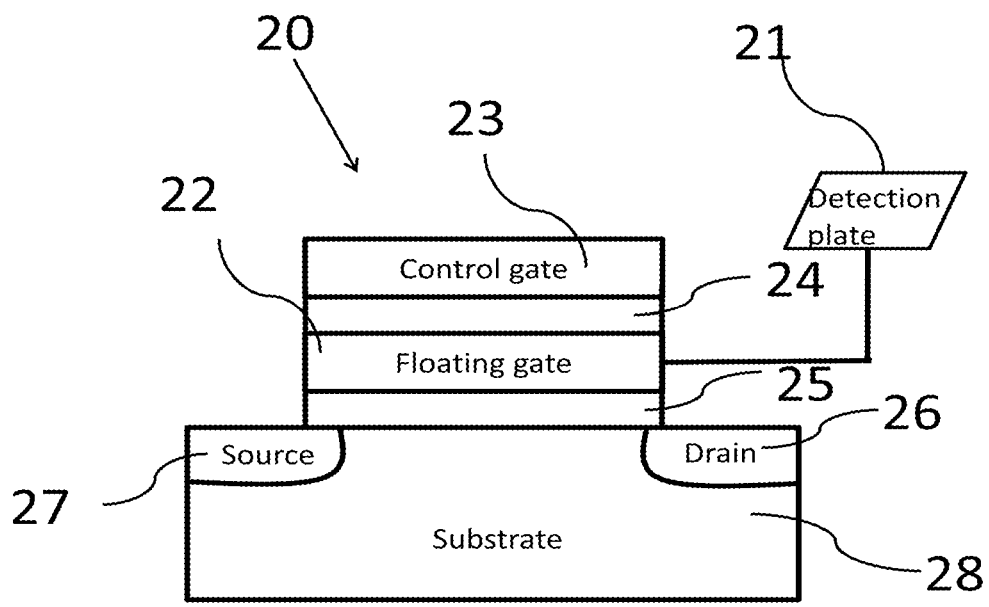
FIG. 2 is a diagram of an example of a double-gate structure of the transistor having a direct-input-type primary input terminal of FIG. 1A, manufactured by an integrated circuit process.

FIG. 2 is a diagram of an example of a double-gate structure of the transistor having a direct-input-type primary input terminal of FIG. 1A, manufactured by an integrated circuit process. The transistor 20 has a double-gate structure and is prepared by the following method: on a substrate 28, two heavily doped regions are generated as a source 27 and a drain 26; the first gate layer is a floating gate 22, a lower portion of which is isolated from the substrate by a dielectric layer 25 and an upper portion of which is isolated from a control gate 23 by another dielectric layer 24; and, the control gate 23 is the second gate layer. This structure is mainly characterized in that the floating gate 22 is connected to a metal wire through a contact hole and then directly drawn to an external detection plate 21. Each of the floating gate 22 and the control gate 23 may be made of any one of polycrystalline silicon, metal, organic conductors and so on. Corresponding to FIG. 1A, the control gate 23 in the transistor 20 serves as a secondary input terminal, the floating gate 22 serves as a primary input terminal, and the detection plate 21 is a detection plate.

Figure 3:
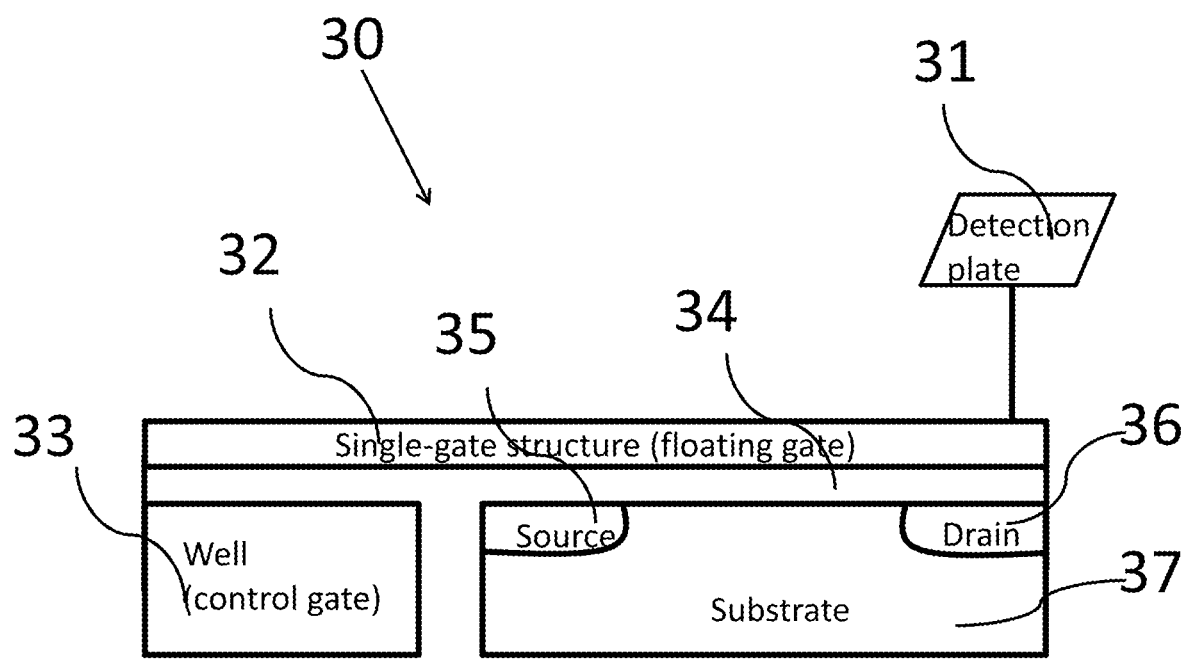
FIG. 3 is a diagram of an example of a single-gate structure of the transistor having a direct-input-type primary input terminal of FIG. 1A, manufactured by an integrated circuit process.

FIG. 3 is a diagram of an example of a single-gate structure of the transistor having a direct-input-type primary input terminal of FIG. 1A, manufactured by an integrated circuit process. The transistor 30 has a single-gate structure and is prepared by the following method: on a substrate 37, two heavily doped regions are generated as a source 35 and a drain 36, a well 33 as a control gate is generated on a side of the substrate 37 by ion implantation; the well 33 and the substrate 37 are arranged in parallel in a gate width direction and should be isolated from each other; a single gate structure 32 is formed above the well 33 and the substrate 37; and, the single-gate structure 32 is isolated from the well 33 and the substrate 37 by a dielectric layer 34. The single-gate structure 32 is connected to a metal wire through a contact hole and then directly drawn to an external detection plate 31. The single-gate structure 32 may be made of any one of polycrystalline silicon, metal, organic conductors and so on. Corresponding to FIG. 1A, the control gate 33 in the transistor 30 serves as a secondary input terminal, the floating gate 32 serves as a primary input terminal, and the detection plate 31 is a detection plate.

Figure 4:
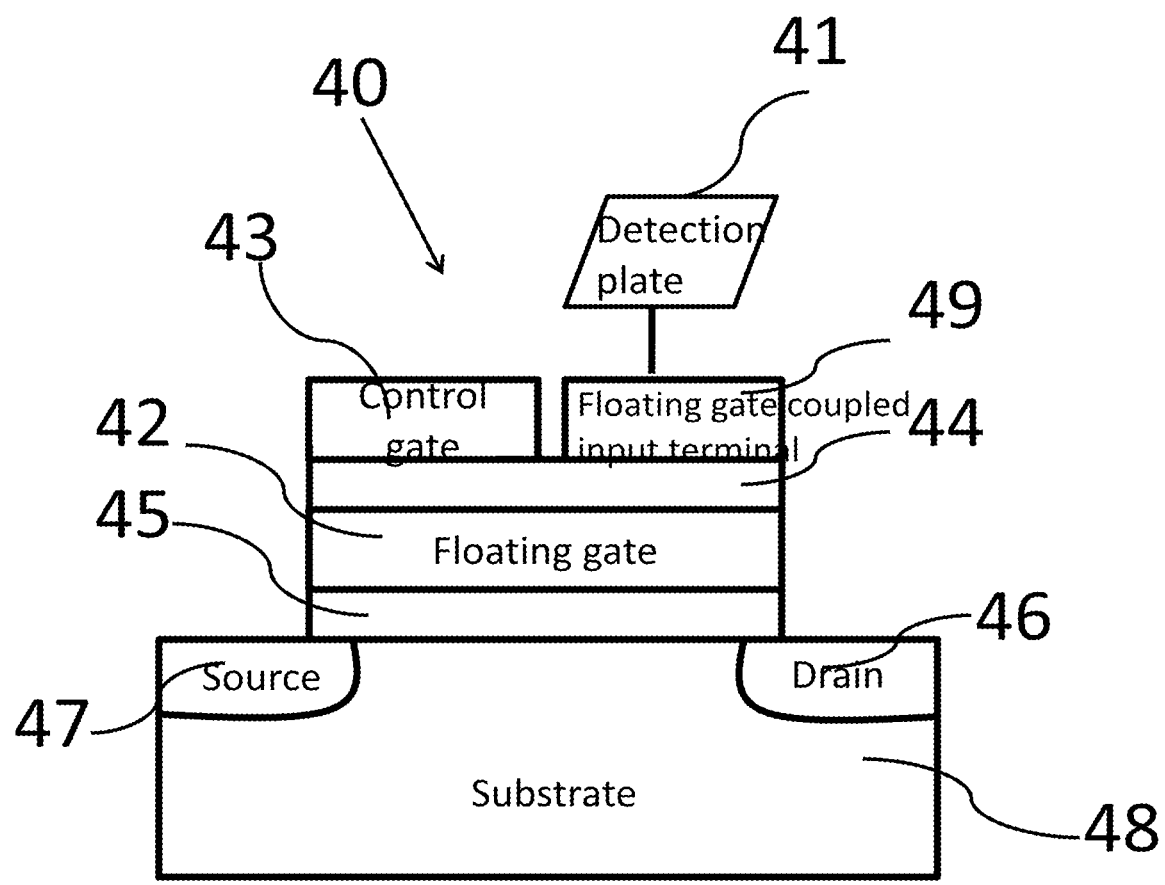
FIG. 4 is a diagram of an example of a double-gate structure of the transistor having a primary input terminal with a capacitor of FIG. 1B, manufactured by an integrated circuit process.

FIG. 4 is a diagram of an example of a double-gate structure of the transistor having a primary input terminal with a capacitor of FIG. 1B, manufactured by an integrated circuit process. The transistor 40 has a double-gate structure and is prepared by the following method: on a substrate 48, two heavily doped regions are generated as a source 47 and a drain 46; the first gate layer is a floating gate 42, a lower portion of which is isolated from the substrate 48 by a dielectric layer 45 and an upper portion of which is isolated from the second gate layer by another dielectric layer 44; and, the second gate layer is a split gate structure, that is, two gates (i.e., a control gate 43 and a floating gate coupled input terminal 49) are manufactured above the floating gate 42, and the two gates are isolated from each other by a dielectric layer. The floating gate coupled input terminal 49 is connected to a metal wire through a contact hole and then directly drawn to an external detection plate 41. Each of the first gate layer and the second gate layer may be made of any one of polycrystalline silicon, metal, organic conductors and so on. Corresponding to FIG. 1B, the control gate 43 in the transistor 40 serves as a secondary input terminal, the floating gate coupled input terminal 49 serves as a primary input terminal, and the detection plate 41 is a detection plate.

Figure 5A:
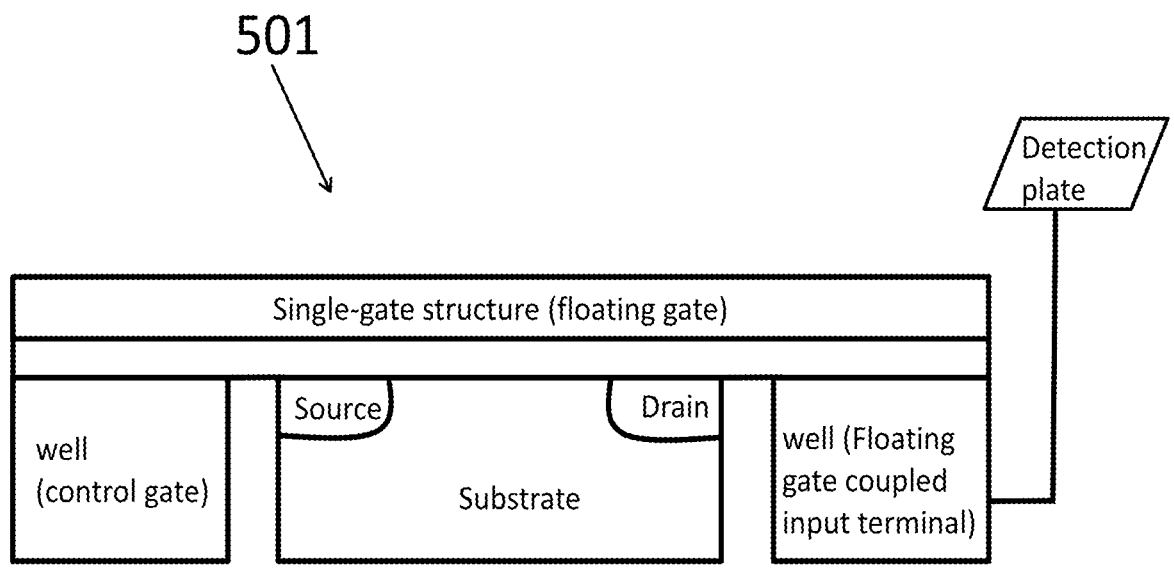
FIGS. 5A-5C are diagrams of an example of a single-gate structure of the transistor having a primary input terminal with a capacitor of FIG. 1B, manufactured by an integrated circuit process.
Figure 5B:
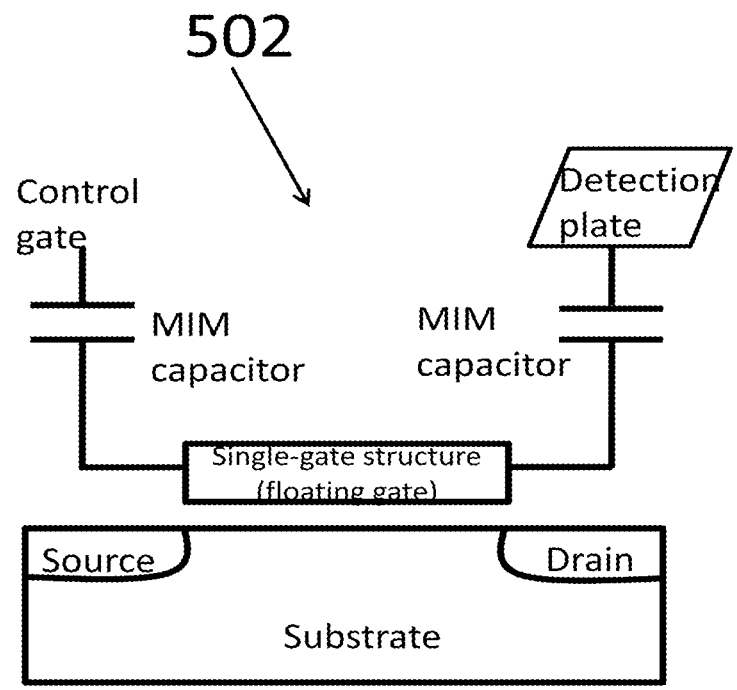
Figure 5C:
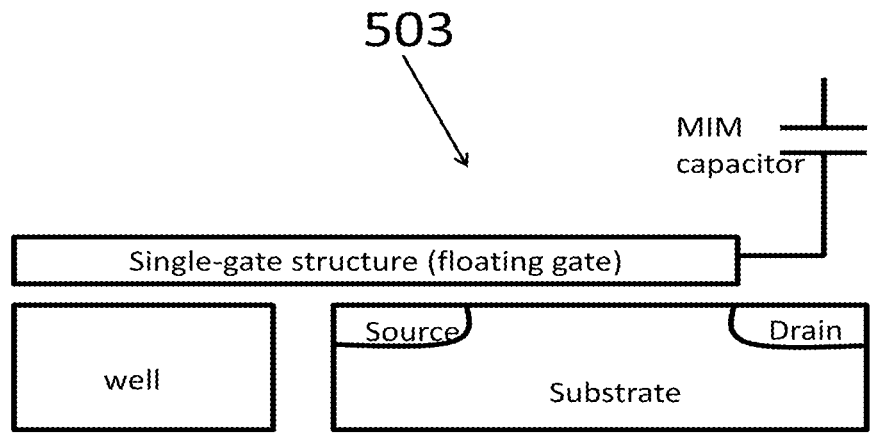

FIGS. 5A-5C are diagrams of an example of a single-gate structure of the transistor having a primary input terminal with a capacitor of FIG. 1B, manufactured by an integrated circuit process, where several methods for preparing a coupling capacitor are mainly shown. In the transistor 501 of FIG. 5A, two wells are used as a control gate and a floating gate coupled input terminal, respectively; in the transistor 502 of FIG. 5B, two metal-insulating layer-metal (MIM) capacitors are used as a control gate and a floating gate coupled input terminal, respectively; and, in the transistor 503 of FIG. 5C, a well and an MIM capacitor are used as a control gate and a floating gate coupled input terminal, respectively, and the both are interchangeable. Corresponding to FIG. 1B, the control gate in each of the three transistors serves as a secondary input terminal, the floating gate coupled input terminal serves as a primary input terminal, and the detection plate is a detection plate. The main bodies of the three transistors are manufactured by a similar process. Two heavily doped regions are generated on the substrate to serve as a source and a drain, the single-gate structure serves as a floating gate, and the floating gate is isolated from the substrate by a dielectric layer. A well capacitor is prepared by the following method: on an extension line in the gate width direction, a well is generated on a side of the substrate by ion implantation, the single-gate structure is extended above the well to form overlap regions with the well, the overlap regions are isolated from each other by a dielectric layer, and the capacitor formed in such a way is a well capacitor. An MIM capacitor is prepared by the following method: two different metal layers are isolated from each other by an insulating layer, and the capacitor formed in such a way is an MIM capacitor.

FIGS. 1A and 1B depict two principles of the core device of the present invention, with the similarity that the transistor is a transistor having at least two input ports and is called a signal superimposable transistor since the two ports are used for superimposing signals, and with the difference that whether the primary input terminal has a coupling capacitor. FIGS. 2 and 3 show implementations of the transistor having a direct-input-type primary input terminal of FIG. 1A under different process conditions, respectively, which can be used for charge detection; and, FIGS. 4-5C show implementations of the transistor having a primary input terminal with a capacitor of FIG. 1B under different process conditions, which can be used for potential detection. It is to be noted that the implementations of the transistors based on the principles of FIGS. 1A and 1B in the present invention are not limited to the solutions in the above implementations.

Figure 6:
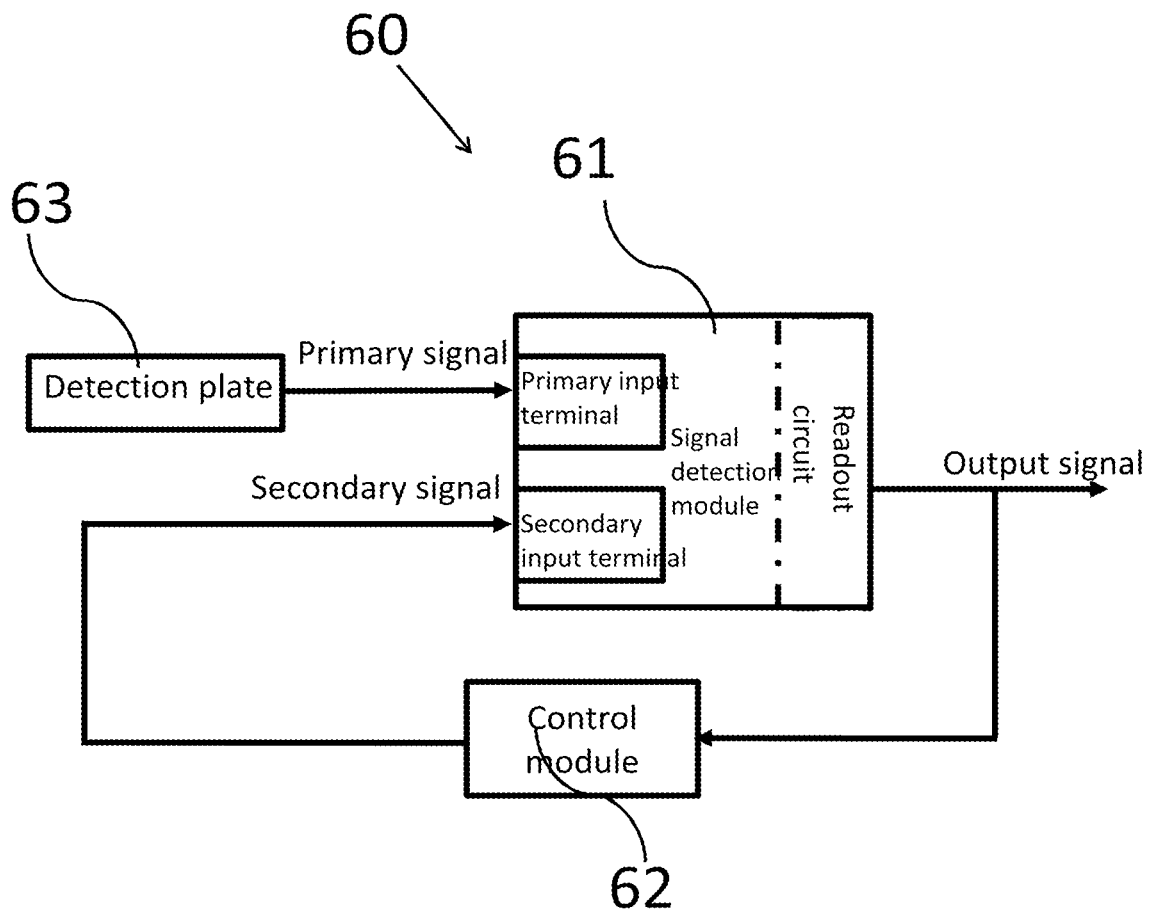
FIG. 6 is a system block diagram of a novel active noise control biosensor according to the present invention.

FIG. 6 is a system block diagram of a novel active noise control biosensor according to the present invention. The novel active noise control biosensor 60 mainly consists of three parts, i.e., a signal detection module 61, a detection plate 63 and a control module 62. The signal detection module 61 consists of a signal superimposable transistor and a readout circuit. The signal superimposable transistor has at least two input terminals, including a secondary input terminal for receiving a secondary signal and a primary input terminal for receiving a primary signal. The secondary input signal and the primary input signal are superimposed in the signal detection module 61 to realize active noise control, and the superimposed signal is read out by the readout circuit in the signal detection module 61 and output as an input signal to the control module 62. The detection plate 63 is connected to a sample to be detected to detect whether the primary signal is input to the primary input terminal of the signal detection module 61. The control module 62 processes an output signal from the signal detection module 61 by a signal processing system to generate and input a secondary signal to the secondary input terminal of the signal detection module 61. The signal superimposable transistor in the signal detection module 61 may be based on any one of the two principles shown in FIGS. 1A and 1B, or may be any one of the transistors described in the above implementations. When the transistor is switched on, the readout circuit may be any one of a source follower amplification circuit, a common source simplification circuit and other simplification and readout circuits. The control module 62 may adapt feedforward control and feedback control. The feedforward control may include reference feedforward control and no-reference feedforward control. The different control modes will be described below in detail.

Figure 7:
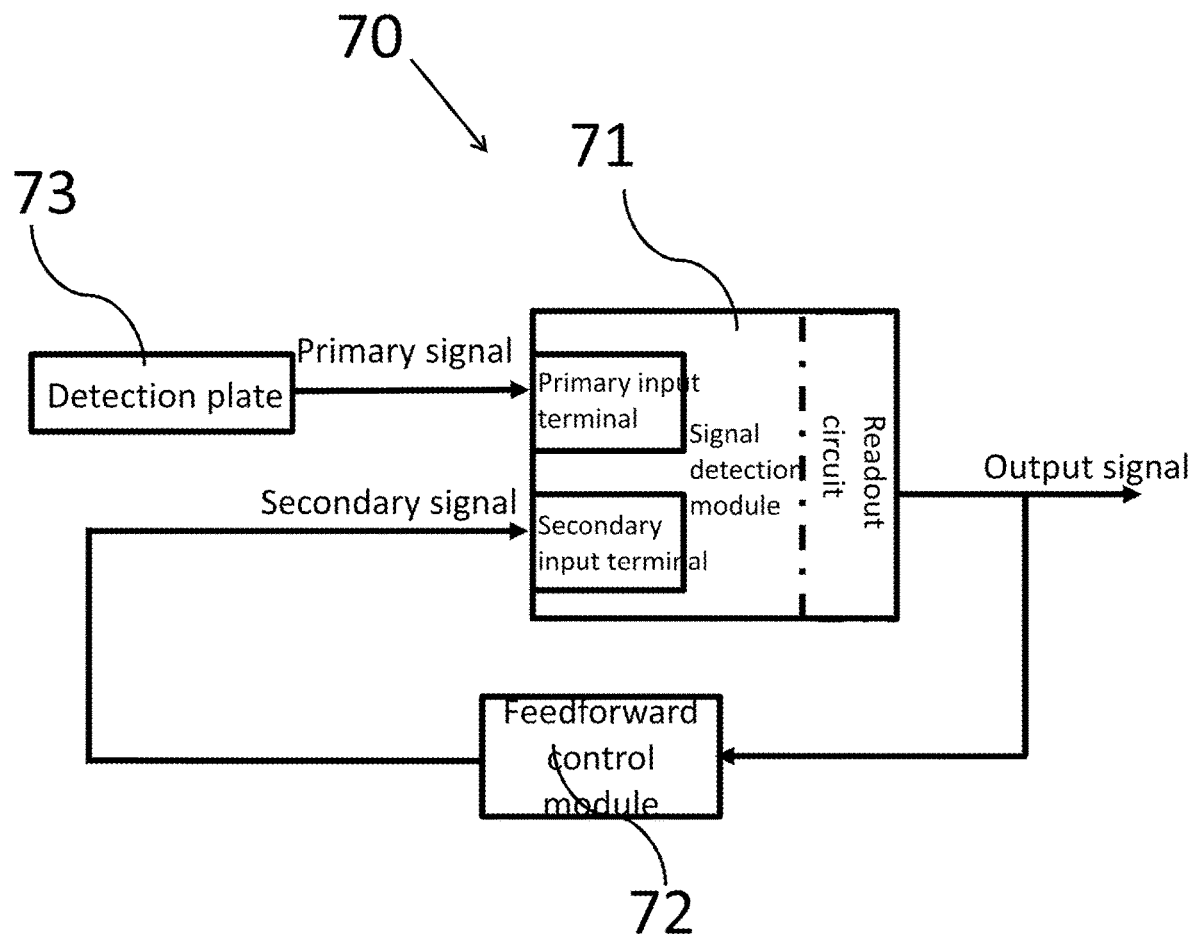
FIG. 7 is a system block diagram of a sensor in which the control module suppresses the known harmonic noise by no-reference feedforward control, according to the present invention.

FIG. 7 is a system block diagram of a sensor in which the control module suppresses the known harmonic noise by no-reference feedforward control, according to the present invention. The sensor 70 mainly consists of a signal detector module 71, a detection plate 73 and a feedforward control module 72. The signal detection module 71 consists of a signal superimposable transistor and a readout circuit. The signal superimposable transistor may be the transistor having a direct-input-type primary input terminal or the transistor having a primary input transistor with a capacitor. The signal superimposable transistor has two input terminals, i.e., a secondary input terminal for receiving a secondary signal and a primary input terminal for receiving a primary signal. The readout circuit reads out signals by any one of a source follower amplification circuit, a common source simplification circuit and other simplification and readout circuits after the transistor is switched on. Under the above readout conditions, an output signal generated by superimposing the input signal of the control gate and the input signal of the floating gate may be read out at the source or the drain of the transistor. The detection plate 73 is connected to a sample to be detected to detect whether the primary signal is input to the primary input terminal of the signal detection module 71. The feedforward control signal 72 may directly generate, by determining primary noise in advance, a harmonic signal having a known frequency inside the control module to serve as a reference for feedforward back control; and, an output signal from the signal detection module 71 is processed by feedforward control to generate and input a secondary signal to the secondary input terminal of the signal detection module 71. The secondary input signal and the primary input signal are superimposed in the signal detection module 71, so that the output noise from the readout circuit in the signal detection module 71 is reduced, and the active noise reduction of the primary harmonic noise is realized. The working condition of such sensors is that the noise needs to be predictable harmonic noise.

Figure 8:
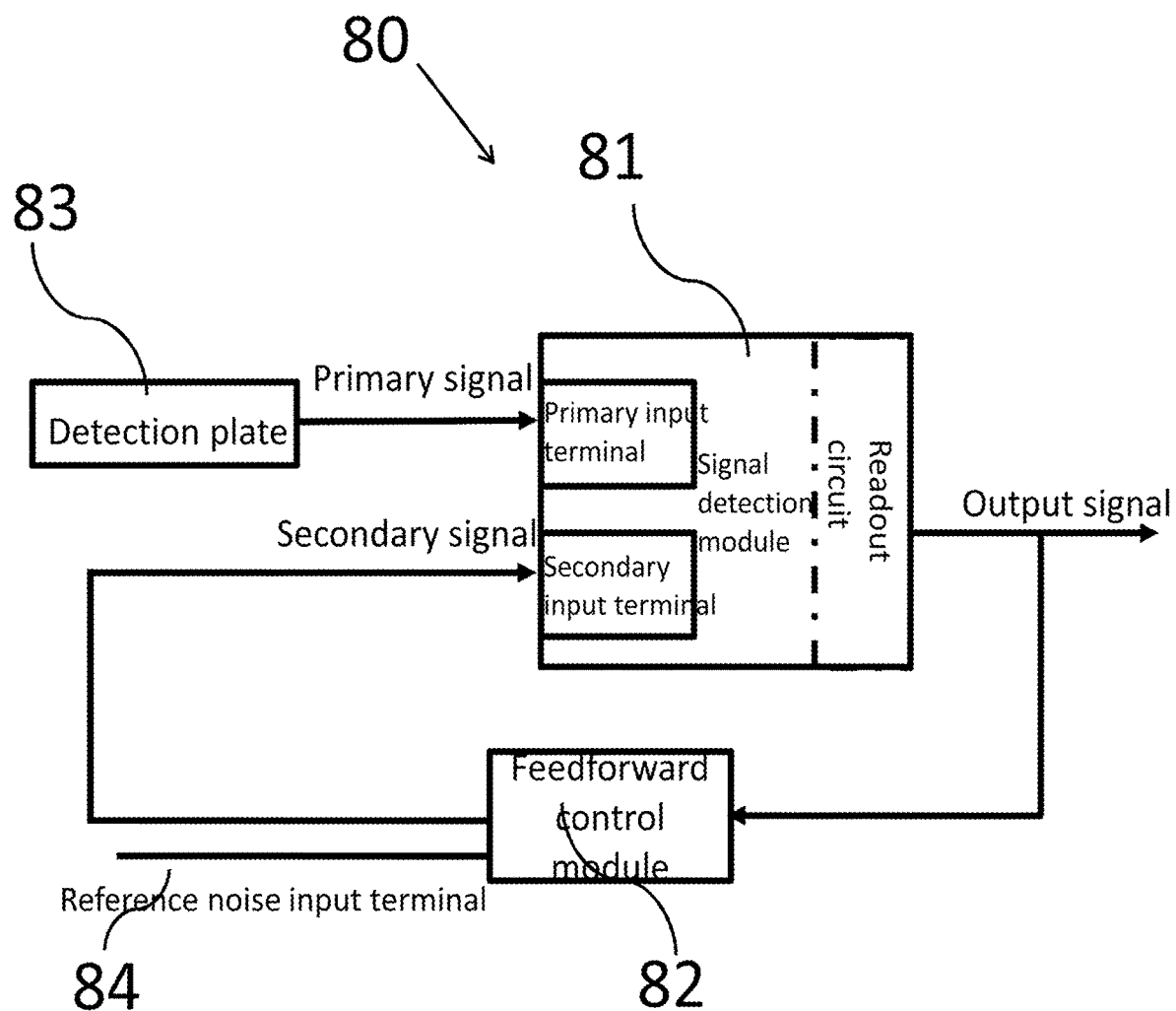
FIG. 8 is a system block diagram of a sensor in which the control module suppresses non-predictable noise by reference feedforward control, according to the present invention.

FIG. 8 is a system block diagram of a sensor in which the control module suppresses non-predictable noise by reference feedforward control, according to the present invention. The constitution and the working principle of the sensor 80 are slightly different from those of the sensor 70. The difference lies in that a reference noise input terminal 84 for detecting background noise as a reference for feedforward control is additionally provided in the feedforward control module 82. The noise signal in the primary signal is an unpredictable signal, including slow DC drift, harmonic waves and broadband noise. The feedforward control module 82 processes an output signal from the signal detection module 81 by feedforward control to generate and input a secondary signal to the secondary input terminal of the signal detection module 81. The signal superimposable transistor in the signal detection module 81 may also be one of the transistor having a direct-input-type primary input terminal and the transistor having a primary input terminal with a capacitor. The readout circuit is the same as that in the sensor 70. The detection plate 83 is connected to a sample to be detected to detect whether the primary signal is input to the primary input terminal of the signal detection module 81. The secondary input signal and the primary input signal are superimposed in the signal detection module 71, so that the output noise from the readout circuit in the signal detection module 81 is reduced, and the active noise reduction of the primary noise is realized.

Figure 9:
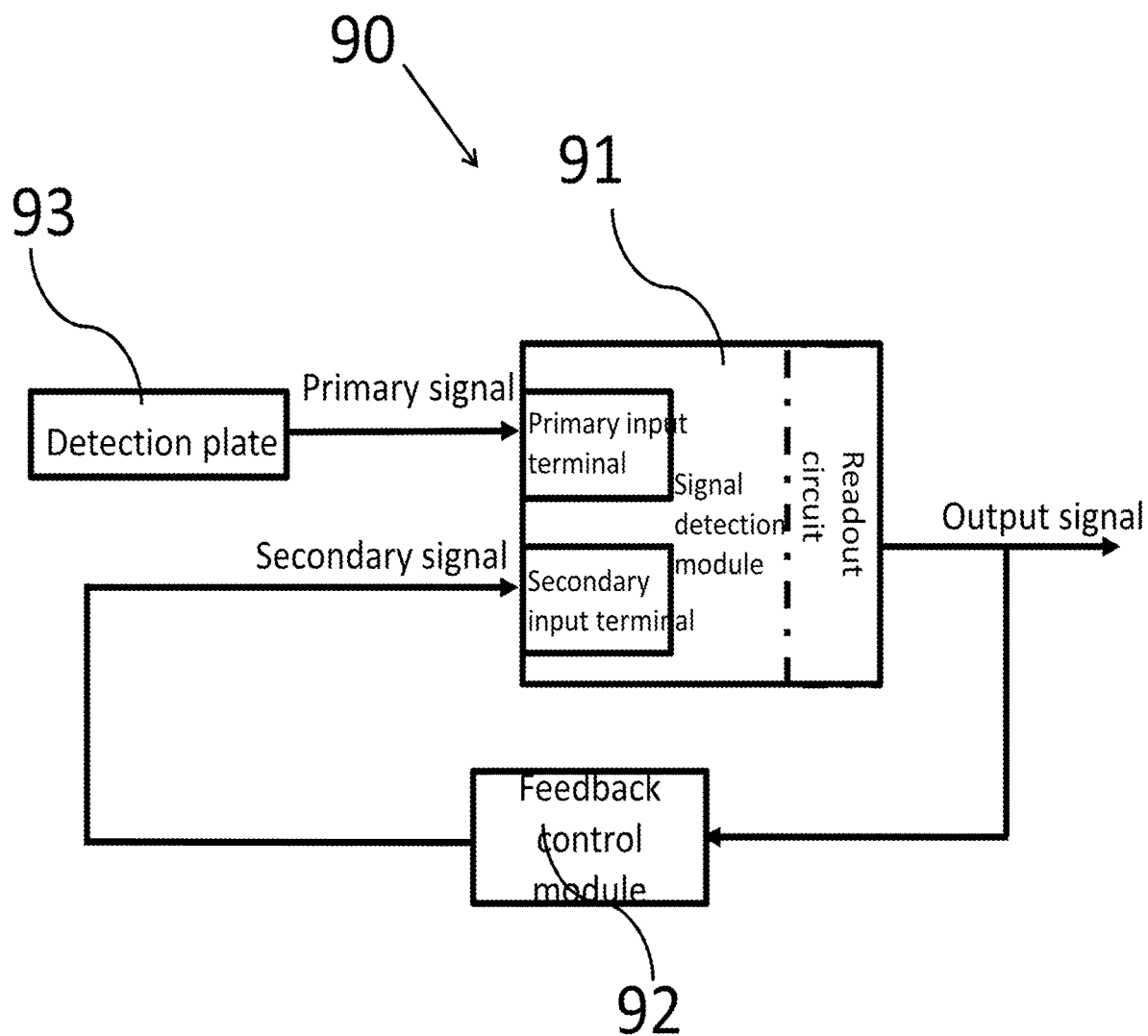
FIG. 9 is a system block diagram of a sensor in which the control module suppresses various kinds of noise by feedback control, according to the present invention.

FIG. 9 is a system block diagram of a sensor in which the control module suppresses various kinds of noise by feedback control, according to the present invention. The difference between the sensor 90 and the sensors 70 and 80 lies in that the sensor 90 uses a feedback control module 92 regardless of the type of the primary noise signal, including slow DC drift, harmonic waves and broadband noise. The signal detection module 91 is identical to the sensor signal detection modules 71 and 81, including identical optionally of the structure of the signal superimposable transistor and identical arrangement of the readout circuit. During the operation, the detection plate 93 is connected to a sample to be detected to detect whether the primary signal is input to the primary input terminal of the signal detection module 91. The readout circuit reads out an output signal and inputs the output signal to the feedback control module 92. An output signal from the signal detection module 91 is processed by feedback control by using the feedback control module 92 to generate and input a secondary signal to the secondary input terminal of the signal detection module 91. Thus, the secondary signal is obtained and input to the secondary input terminal of the signal detection module 91. The secondary input signal and the primary input signal are superimposed in the signal detection module 91, so that the output noise from the readout circuit in the signal detection module 91 is reduced, and the active noise reduction of the primary noise is realized.

Figure 10:
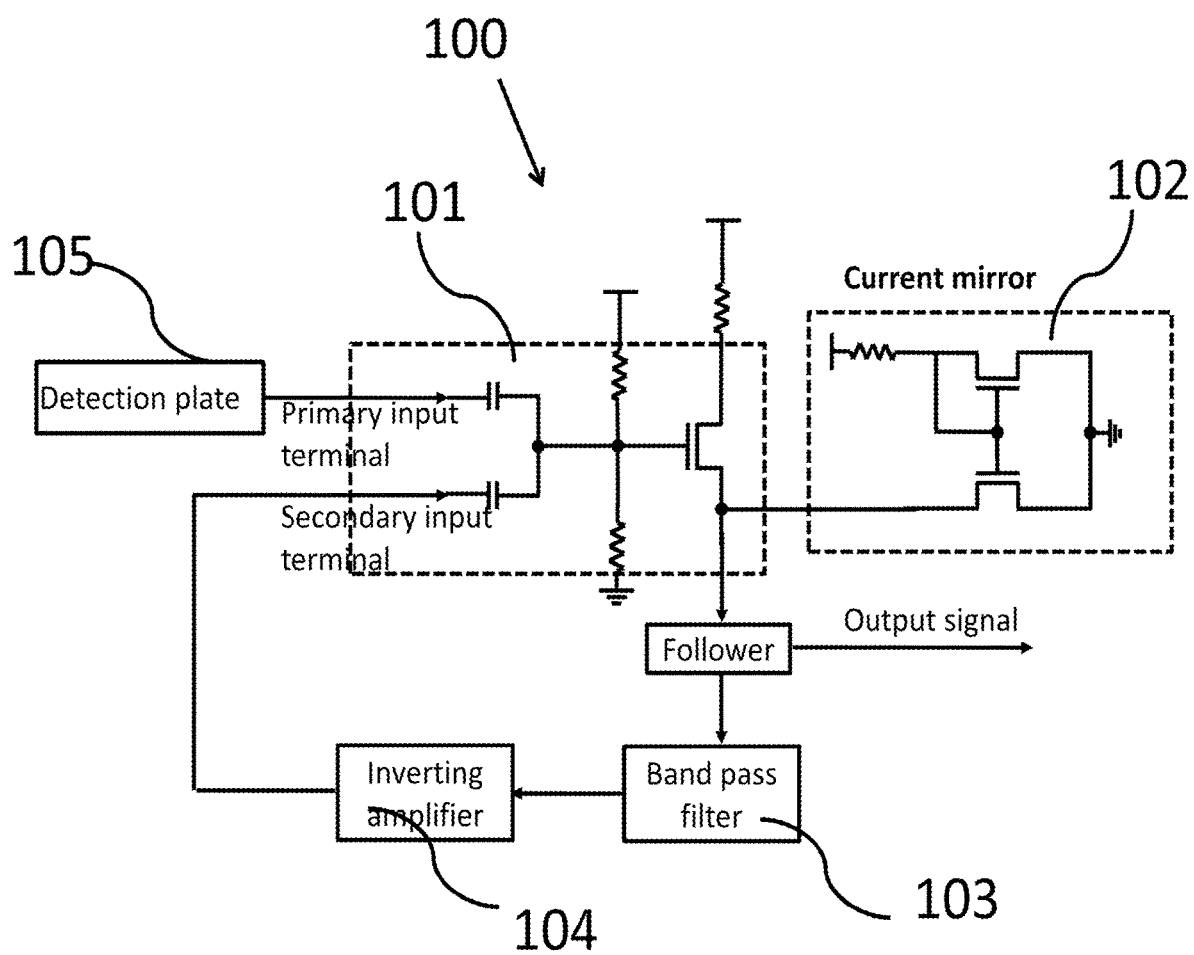
FIG. 10 is a diagram showing an implementation of a sensor for suppressing power frequency interference based on the system of FIG. 9.

FIG. 10 is an implementation of the sensor 90 of FIG. 9. The sensor 100 is aimed at suppressing 50 Hz power frequency interference in the primary signal, that is, the primary noise is 50 Hz power frequency interference. The sensor 100 is based on the principle of the transistor having a primary input terminal with a capacitor in FIG. 1B. The signal superimposable transistor 101 may be a field effect transistor having two capacitors at its gate. One capacitor is a capacitor at the primary input terminal and connected to the detection plate 105, and the other capacitor is a control gate capacitor. The readout circuit is specifically implemented as follows: a turn-on voltage is applied to the control gate and a positive voltage is applied to the drain to ensure that the transistor is in a saturated operating area; and, the source is connected to a current mirror 102 to realize source follower output, so that the output signal from the source changes with the change in voltage signal on the floating gate. The voltage signal detected by the detection plate 105 is input to the gate of the transistor through the capacitor at the primary input terminal, and a signal is output by the readout signal. The output signal is processed by the feedback control module to generate a secondary signal, and the secondary signal is input to the secondary input terminal of the transistor. The primary input signal and the secondary input signal are superimposed in the transistor to realize active noise reduction. The feedback control module of the sensor 100 includes a band pass filter 103 at a center frequency of 50 Hz and an inverting amplifier. The noise suppression effect may be adjusted by adjusting the center frequency and quality factor of the band pass filter and the gain of the inverting amplifier.

The invention claimed is:

1. A novel active noise control biosensor, comprising a detection plate, a signal detection module and a control module, characterized in that the signal detection module comprises a signal superimposable transistor and a readout circuit; the signal superimposable transistor has at least two input terminals, including a secondary input terminal for receiving a secondary signal and a primary input terminal for receiving a primary signal; the detection plate inputs a detected primary signal to the primary input terminal, and the control module processes an output signal from the signal detection module by a signal processing system and generates and inputs a secondary signal to the secondary input terminal; and, the primary signal and the secondary signal received by the signal superimposable transistor are superimposed to realize active noise control, and the superimposed signal is read out by the readout circuit and output as an input signal to the control module.

2. The novel active noise control biosensor according to claim 1, characterized in that a gate of the signal superimposable transistor is connected to a capacitor and a metal wire serving as a secondary input terminal and a primary input terminal; or, the gate of the transistor is connected to two capacitors serving as a primary input terminal a secondary input terminal.

3. The novel active noise control biosensor according to claim 1, characterized in that the signal superimposable transistor is a field effect transistor.

4. The novel active noise control biosensor according to claim 1, characterized in that, on a substrate of the signal superimposable transistor, two heavily doped regions are generated as a source and a drain, respectively; a double-gate structure is provided above the substrate, the first gate layer is a floating gate and the second gate layer is a control gate; the lower portion of the floating gate is isolated from the substrate by a dielectric layer, while the upper portion thereof is isolated from the control gate by another dielectric layer; and, the floating gate is connected to the detection plate by a metal wire to serve as a primary input terminal, and the control gate serves as a secondary input terminal.

5. The novel active noise control biosensor according to claim 1, characterized in that, on a substrate of the signal superimposable transistor, two heavily doped regions are generated as a source and a drain, respectively; a double-gate structure is provided above the substrate, the first gate layer is a floating gate, and the second gate layer is a split gate structure including a control gate and a floating gate coupled input terminal between which an isolation layer is provided; a lower portion of the floating gate is isolated from the substrate by a dielectric layer while an upper portion thereof is isolated from the second gate layer by another dielectric layer; and, the floating gate coupled input terminal is connected to the detection plate by a metal wire to serve as a primary input terminal, and the control gate serves as a secondary input terminal.

6. The novel active noise control biosensor according to claim 1, characterized in that, on a substrate of the signal superimposable transistor, two heavily doped regions are generated as a source and a drain, respectively; a single-gate structure as a floating gate is provided above the substrate; the floating gate is isolated from the substrate by a dielectric layer; the floating gate is connected to two metal-insulating layer-metal capacitors serving as a primary input terminal and a secondary input terminal.

7. The novel active noise control biosensor according to claim 1, characterized in that, on a substrate of the signal superimposable transistor, two heavily doped regions are generated as a source and a drain, respectively; a single-gate structure as a floating gate is provided above the substrate; a well is generated on a side of the substrate in a gate width direction; an isolation layer is provided between the substrate and the well, and the floating gate is isolated from the well and the substrate by a dielectric layer; the well serves as a secondary input terminal and the floating gate is connected to the detection plate by a metal wire to serve as a primary input terminal; or, the well serves as a secondary input terminal and the floating gate is connected to a metal-insulating layer-metal capacitor to serve as a primary input terminal; or, the well serves as a primary input terminal and the floating gate is connected to a metal-insulating layer-metal capacitor to serve as a secondary input terminal.

8. The novel active noise control biosensor according to claim 1, characterized in that, on a substrate of the signal superimposable transistor, two heavily doped regions are generated as a source and a drain, respectively; a single-gate structure as a floating gate is provided above the substrate; two wells are generated on a side of the substrate in a gate width direction to serve as a control gate and a floating gate coupled input terminal, respectively; an isolation layer is provided between the substrate and the wells, and the floating gate is isolated from the wells and the substrate by a dielectric layer; and, the floating gate coupled input terminal is connected to the detection plate by a metal wire to serve as a primary input terminal, and the control gate serves as a secondary input terminal.

9. The novel active noise control biosensor according to claim 1, characterized in that the control module is a no-reference feedforward control module, that is, a harmonic signal having a known frequency is directly generated inside the control module as a reference for feedforward control, and an output signal from the signal detection module is processed by feedforward control to generate and input a secondary input signal to the secondary input terminal of the signal detection module;

or, the control module is a reference feedforward control module, that is, a reference noise input terminal is drawn from the control module to detect background noise as a reference for feedforward control, and an output signal from the signal detection module is processed by feedforward control to generate and input a secondary input signal to the secondary input terminal of the signal detection module;

or, the control module is a feedback control module, and an output signal from the signal detection module is processed by feedback control to generate and input a secondary signal to the secondary input terminal of the signal detection module.

10. The novel active noise control biosensor according to claim 2, characterized in that the signal superimposable transistor is a field effect transistor.

11. The novel active noise control biosensor according to claim 2, characterized in that, on a substrate of the signal superimposable transistor, two heavily doped regions are generated as a source and a drain, respectively; a double-gate structure is provided above the substrate, the first gate layer is a floating gate and the second gate layer is a control gate; the lower portion of the floating gate is isolated from the substrate by a dielectric layer, while the upper portion thereof is isolated from the control gate by another dielectric layer; and, the floating gate is connected to the detection plate by a metal wire to serve as a primary input terminal, and the control gate serves as a secondary input terminal.

12. The novel active noise control biosensor according to claim 2, characterized in that, on a substrate of the signal superimposable transistor, two heavily doped regions are generated as a source and a drain, respectively; a double-gate structure is provided above the substrate, the first gate layer is a floating gate, and the second gate layer is a split gate structure including a control gate and a floating gate coupled input terminal between which an isolation layer is provided; a lower portion of the floating gate is isolated from the substrate by a dielectric layer while an upper portion thereof is isolated from the second gate layer by another dielectric layer; and, the floating gate coupled input terminal is connected to the detection plate by a metal wire to serve as a primary input terminal, and the control gate serves as a secondary input terminal.

13. The novel active noise control biosensor according to claim 2, characterized in that, on a substrate of the signal superimposable transistor, two heavily doped regions are generated as a source and a drain, respectively; a single-gate structure as a floating gate is provided above the substrate; the floating gate is isolated from the substrate by a dielectric layer; the floating gate is connected to two metal-insulating layer-metal capacitors serving as a primary input terminal and a secondary input terminal.

14. The novel active noise control biosensor according to claim 2, characterized in that, on a substrate of the signal superimposable transistor, two heavily doped regions are generated as a source and a drain, respectively; a single-gate structure as a floating gate is provided above the substrate; a well is generated on a side of the substrate in a gate width direction; an isolation layer is provided between the substrate and the well, and the floating gate is isolated from the well and the substrate by a dielectric layer; the well serves as a secondary input terminal and the floating gate is connected to the detection plate by a metal wire to serve as a primary input terminal; or, the well serves as a secondary input terminal and the floating gate is connected to a metal-insulating layer-metal capacitor to serve as a primary input terminal; or, the well serves as a primary input terminal and the floating gate is connected to a metal-insulating layer-metal capacitor to serve as a secondary input terminal.

15. The novel active noise control biosensor according to claim 2, characterized in that, on a substrate of the signal superimposable transistor, two heavily doped regions are generated as a source and a drain, respectively; a single-gate structure as a floating gate is provided above the substrate; two wells are generated on a side of the substrate in a gate width direction to serve as a control gate and a floating gate coupled input terminal, respectively; an isolation layer is provided between the substrate and the wells, and the floating gate is isolated from the wells and the substrate by a dielectric layer; and, the floating gate coupled input terminal is connected to the detection plate by a metal wire to serve as a primary input terminal, and the control gate serves as a secondary input terminal.

16. The novel active noise control biosensor according to claim 2, characterized in that the control module is a no-reference feedforward control module, that is, a harmonic signal having a known frequency is directly generated inside the control module as a reference for feedforward control, and an output signal from the signal detection module is processed by feedforward control to generate and input a secondary input signal to the secondary input terminal of the signal detection module;

or, the control module is a reference feedforward control module, that is, a reference noise input terminal is drawn from the control module to detect background noise as a reference for feedforward control, and an output signal from the signal detection module is processed by feedforward control to generate and input a secondary input signal to the secondary input terminal of the signal detection module;

or, the control module is a feedback control module, and an output signal from the signal detection module is processed by feedback control to generate and input a secondary signal to the secondary input terminal of the signal detection module.

* * * * *